United States Patent [19]

Komatsu et al.

[11] 4,320,141

[45] Mar. 16, 1982

[54] ANTITUMOR AGENT

[76] Inventors: Yasuhiro Komatsu; Michiko Nagai, both of c/o Nisshin Flour Milling Co., Ltd. Central Research Institute, 177-3, Ohaza-Tsurugaoka, Ohi-machi, Iruma-gun, Saitama-ken, Japan

[21] Appl. No.: 154,415

[22] PCT Filed: Dec. 14, 1978

[86] PCT No.: PCT/JP78/00055

§ 371 Date: Aug. 16, 1979

§ 102(e) Date: Aug. 16, 1979

[87] PCT Pub. No.: WO79/00401

PCT Pub. Date: Jul. 12, 1979

[30] Foreign Application Priority Data

Dec. 16, 1977 [JP] Japan ................................ 52/150626
Dec. 29, 1977 [JP] Japan ................................ 52/157630

[51] Int. Cl.$^3$ ............................................ C07D 311/70
[52] U.S. Cl. ................................ 424/284; 260/345.5; 542/426

[58] Field of Search ..................... 542/426; 260/345.5; 424/284

[56] References Cited

U.S. PATENT DOCUMENTS

| 2,231,125 | 2/1941 | Karrer | 260/345.5 |
| 3,151,127 | 9/1964 | Spaivel | 260/345.4 |
| 3,878,202 | 4/1975 | Fukawa et al. | 260/345.5 |

OTHER PUBLICATIONS

Komatsu et al., Chem. Abstracts, 89 (1978), #100352.
The Merck Index, 7th edition, Merck and Co., N.J. p. 1097.

*Primary Examiner*—Arthur P. Demers
*Attorney, Agent, or Firm*—Abelman, Frayne & Rezac

[57] ABSTRACT

This invention relates to an antitumor agent comprising as the active ingredient α-tocopherol vitamin A acid ester and to novel α-tocopherol-13-cis-vitamin A acid ester. Vitamin A acid has heretofore been known to possess antitumor activity but it is defective in that its toxicity is extremely high. The active ingredient of this invention is characterized by its high antitumor activity and extremely low toxicity.

2 Claims, No Drawings

ANTITUMOR AGENT

TECHNICAL FIELD

This invention relates to an antitumor agent containing as the active ingredient an α-tocopherol vitamin A acid ester. Further, this invention relates to novel compound, α-tocopherol-13-cis-vitamin A acid ester.

BACKGROUND ART

Vitamin A acid has already been known to possess antitumor activity and recognized as being effective for prophylaxis of development or therapy of experimental tumor developed on epithelial cells. However, the vitamin A acid is quite strongly toxic and due to this properties, vitamin A acid has not been brought into practice up to now as an antitumor agent.

DISCLOSURE OF INVENTION

As a result of our extensive researches with a view to overcoming defects according to prior arts, we found that α-tocopherol vitamin A acid ester (chemical nomenclature: tocopheryl retinoate) possesses the antitumor activity and shows very low toxicity.

The term α-tocopherol as used in this invention indicates dl-α-tocopherol or d-α-tocopherol and the term vitamin A acid indicates one in the all trans-form or 13-cis-form. Vitamin A acid ester of 13-cis-form is a novel compound and a process for the preparation thereof is explained below. Such process includes a process which comprises subjecting both 13-cis-vitamin A acid and α-tocopherol used as the starting materials to ester linkage or a process which comprises converting all trans-form vitamin A acid ester into 13-cis-form ester by isomerization. The process comprising formation of ester linkage may be carried out according to a known ester formation reaction, for example, the process described in Japanese Pat. No. 26632/1974. As the process for the isomerization, there can be applied a known photoisomerization process for carotenoids.

Acute toxicity in mice of α-tocopherol vitamin A acid ester which is the active ingredient of the antitumor agent of this invention is particularly low as shown below, even when any route of administration such as oral route, intraperitoneal route or intravenous injection is applied.

|  | LD$_{50}$ Values in Mice | | |
|---|---|---|---|
|  | Oral administration | Intraperitoneal administration | Intravenous injection |
| α-Tocopherol-trans-vitamin A acid ester | more than 10g/kg | more than 10g/kg | more than 1g/kg |
| α-Tocopherol-13-cis-vitamin A acid ester | more than 10g/kg | more than 10g/kg | more than 1g/kg |
| Vitamin A acid | 780mg/kg | 150mg/kg | 92mg/kg |

Physiological activities of the α-tocopherol vitamin A acid ester used in the present invention as the active ingredient are shown below.

(1) Prophylactic effect on development of tumor

To groups of 10 ICR mice, was applied 0.2% acetone solution of a cancerigenic agent, dimethylbenzanthracene (abbreviated hereinafter as DMBA) by coating said solution on the depilated back of the mice once a day for two weeks. From one week after the final administration of DMBA, an acetone solution of 0.06% croton oil and a lotion containing an acetone solution of 0.06% croton oil and the active ingredient according to the present invention were coated successively on the back once a day for 4 months.

The lotion used above was prepared according to the following process:

A desired amount of α-tocopherol vitamin A acid ester was dissolved in 10 g of ethyl alcohol together with 0.5 g of polyoxymethylene sorbitan monolaurate and 6 g of glycerin and purified water were added thereto to make up the total 100 g. The solution thus obtained was stirred thoroughly to give lotion.

Test results obtained are shown below in table.

| Treatment | Administration route | Number of animals in which tumor was developed |
|---|---|---|
| Control |  | 0 |
| 0.3% Lotion of α-tocopherol-trans-vitamin A acid ester | percutaneous | 0 |
| 0.3% Lotion of α-tocopherol-13-cis-vitamin A acid ester | " | 0 |
| Croton oil | " | 10 |
| Croton oil + 0.02% Lotion of α-tocopherol-trans-vitamin A acid ester | " | 5 |
| Croton oil + 0.3% Lotion of α-tocopherol-trans-vitamin A acid ester | " | 2 |
| Croton oil + 0.02% Lotion of α-tocopherol-13-cis-vitamin A acid ester | " | 4 |
| Croton oil + 0.3% Lotion of α-tocopherol-13-cis-vitamin A acid ester | " | 2 |
| Croton oil + 200mg/day of α-tocopherol-trans-vitamin A acid ester | oral | 3 |

As apparent from the above test results, animals to which croton oil was administered showed development of tumor attributable to the secondary stimulation of the croton oil, whereas animals to which both croton oil and the active ingredient according to the present invention were simultaneously administered were outstandingly inhibited in the development of tumor. Thus, it is clear that the active ingredient of the present invention prevents development of tumor.

(2) Therapeutic effect on tumor

On the back of hairless mice was coated 0.2% DMBA dissolved in olive oil with a brush three times a week for 2 months. After confirmation of development of tumor, test zone comprising groups of five mice was arranged indiscriminately. To these animals was administered α-tocopherol vitamin A acid ester either topically or orally and change of tumor was observed. Three weeks after the administration, the states of tumor were as shown in table below.

| Treatment | Average number of tumor*[1] | | | Administration route |
|---|---|---|---|---|
|  | larger than 5mm | 5–2mm | smaller than 2mm |  |
| Control | 17 | 8 | 5 | topical*[2] |
| 0.01% Lotion of α-tocopherol-trans-vitamin A acid ester | 7 | 5 | 8 | " |
| 0.05% Lotion of α-tocopherol-trans-vitamin A acid ester | 1 | 6 | 13 | " |

| Treatment | Average number of tumor[1] | | | Administration route |
|---|---|---|---|---|
| | larger than 5mm | 5–2mm | smaller than 2mm | |
| 0.01% Lotion of α-tocopherol-13-cis-vitamin A acid ester | 4 | 3 | 8 | " |
| 0.05% Lotion of α-tocopherol-13-cis-vitamin A acid ester | 2 | 6 | 4 | " |
| 200mg/kg of α-tocopherol-trans-vitamin A acid ester | 4 | 6 | 10 | oral |
| 500mg/kg of α-tocopherol-trans-vitamin A acid ester | 2 | 5 | 6 | " |

[1]Average number of tumor counted on each animal
[2]All the topical administrations were effected by coating lotion on the back of animal twice a day with brush.

As apparent from the above test results, the active ingredient of this invention can be administered in such manner as topical coating, oral administration, injection or the like. For use in adult therapy, the active ingredient of this invention is administered in an amount of 100–1200 mg/day and when used in the form of a topicum such as lotion, it is desirable to coat such topicum as containing 0.01–0.5% of the effective component topically several times a day.

Specific examples of the pharmaceutical preparations according to the present invention will be explained below.

When the active ingredient of this invention is to be administered orally, it may be formulated as tablets, granules or powders and, in particular, granules and powders can be made, if necessary, in a unit dose form such as capsules. These solid preparations used for oral administration may contain ordinary excipient, for example, anhydrous silicic acid, metasilicic acid, magnesium aluminate, synthetic aluminum silicate, lactose, sugar, corn starch, fine crystal cellulose, hydroxypropyl starch or glycine; binder, for example, gum arabic, gelatin, tragacanth, hydroxypropyl cellulose or polyvinyl pyrrolidone; lubricant, for example, magnesium stearate, talc or silica; disintegrator, for example, potato starch, carboxymethyl cellulose calcium; or moistening agent, for example, polyethylene glycol, sorbitan monooleate, polyoxyethylene-hardened castor oil or sodium laurylsulfate. Tablets may be subjected to coating according to an ordinary method.

Liquid pharmaceutical preparations for oral use may be formulated in the form of an aqueous or oily emulsion solution, syrup or the like, or alternatively, a dry product which can be redissolved with an appropriate vehicle immediately before use may be formulated. To these liquid pharmaceutical preparations, there may be added such additives as ordinarily used, for example, emulsification aid i.e. sorbitol syrup, methyl cellulose, gelatin, hydroxyethyl cellulose, etc.; emulsifier, for example, lecithin sorbitan monooleate; polyoxyethylenehardened castor oil; non-aqueous vehicle, for example, fractionated coconut oil, almond oil, peanut oil; preservative, for example, methyl p-hydroxybenzoate, propyl p-hydroxybenzoate or sorbic acid.

Further, to the above-mentioned pharmaceutical preparations used for oral administration, there may be included, if necessary, a conservative or stabilizer.

When the active ingredient of this invention is used as an injection, it may be formulated in such form as an oil solution, emulsion or aqueous solution and these solutions may contain an emulsifier, stabilizer or the like as ordinarily used. The above compositions can contain depending upon the route for administration thereof more than 1%, preferably 5–50% of the active ingredient of this invention.

OPTIMUM EMBODIMENT FOR PRACTICE OF THIS INVENTION

Preparation Example 1

1 g Of 13-cis-vitamin A acid and 1.5 g of α-tocopherol are dissolved in 10 cc of dry tetrahydrofuran and 0.9 g of trifluoroacetic acid anhydride dissolved in 5 cc of dry tetrahydrofuran is slowly added dropwise at 0° C. with stirring under nitrogen gas stream. After completion of the addition, the reaction mixture is allowed to further react for 2 hours at room temperature. Thereafter, the reaction mixture is taken into ice-water and then extracted with 20 cc of ether. The ether layer is washed subsequently with water, dilute alkali, water and saturated aqueous salt solution and then dried over magnesium sulfate and ether is distilled off to afford 2.4 g of oily yellow product. This product is subjected to 20 g of silica gel column and eluted with hexane:ether of 50:1 to give oily yellow α-tocopherol-13-cis-vitamin A acid ester of the formula

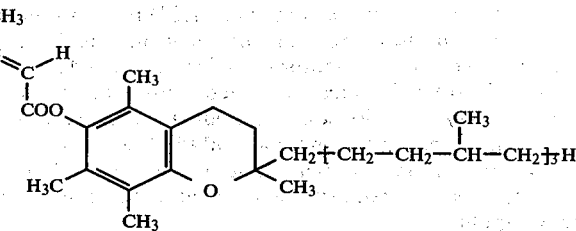

Yield: 1.73 g (73%)
Physical properties of the above product are as follows: UV and visible part absorption spectrum:

| $\lambda_{max}$ | 367nm | $E\,^{1\%}_{1cm} = 533.7$ (EtOH) |
|---|---|---|
| $\lambda_{shoulder}$ | 288nm | $E\,^{1\%}_{1cm} = 122.0$ (EtOH) |

IR $\nu^{Film}_{max}$ (cm$^{-1}$)

2920 1720 1600 1590 1450 1230 1130 980

NMR δ values:
7.8 (1H d 12-position )
6.98 (1H d-d 11-position )
6.13 (3H m 7-, 8-, 10-position )

| | |
|---|---|
| 5.9 | (1H s 14-position $\underset{H}{\underset{|}{\diagdown}}$) |
| 2.6 | (2H t benzyl position in tocopherol moiety $H\underset{}{\diagdown}\diagup H$) |
| 2.16 | (13-position $\underset{}{\diagdown}\underset{CH_3}{|}$) |
| 2.1, 2.0 | (tocopherol moiety $\text{benzene}-(CH_3)_3$) |
| 2.0 | |
| 2.0 | (9-position $\underset{}{\diagdown}\underset{CH_3}{|}$) |
| 1.22 | (tocopherol moiety $\diagup CH_2 \diagdown$ and $\diagup O \diagdown \underset{CH_3}{|}$) |
| 1.0 | (1-position $CH_3 \diagdown \diagup CH_3$) |
| 0.85 | (tocopherol moiety $\underset{H}{\underset{|}{\diagdown}}\underset{CH_3}{|}$) |

Elementary analysis (for $C_{49}H_{76}O_3$): Calc'd. C: 82.53% H: 10.74%. Found C: 82.47% H: 10.75%.

TLC (silica gel plate manufactured by Merck)

$R_f$ value 0.63 (hexane:benzene=1:1)

(For reference: trans AE 0.47)

PREPARATION EXAMPLE 2

2 g Of α-tocopherol are dissolved in a mixed solution of 10 cc of dry benzene and 1 cc of pyridine and 1.3 g of 13-cis-vitamin A acid chloride dissolved in 3 cc of dry benzene are slowly added dropwise with stirring at 0° C. under nitrogen gas stream. After completion of the addition, the reaction mixture is allowed to further react for 5 hours at room temperature. Thereafter, the reaction mixture is taken into ice-water and then extracted with 15 cc of ether. The ether extract is washed subsequently with water, diluted hydrochloric acid, dilute alkali and saturated aqueous salt solution and thereafter dried over magnesium sulfate and ether is distilled off. The residue is purified similarly as in Example 1 by being subjected to 30 g of silica gel column. Oily yellow α-tocopherol-13-cis-vitamin A acid ester is obtained.

Yield: 1.45 g (65%)

The acid chloride can be prepared according to the following process:

2 g Of 13-cis-vitamin A acid are dissolved in 10 cc of dry benzene and 1.3 cc of 28% MeONa solution in MeOH is added. Thereafter, the solvent is distilled off to give sodium salt of 13-cis-vitamin A acid. This salt is suspended again in 10 cc of dry benzene and 0.5 cc of pyridine is added. Under cooling with ice, 0.9 g of oxalyl chloride is added dropwise with stirring. After completion of the addition, stirring is continued for further 2 hours and the resulting NaCl is separated by filtration. Then, the solvent is distilled off and the residue is used directly for the subsequent esterification reaction.

Crude yield: 2.2 g

PREPARATION EXAMPLE 3

1 g Of α-tocopherol vitamin A acid ester of all transform is dissolved in 100 cc of special grade acetone and the resulting solution is subjected to sun light irradiation for 4 hours. Acetone is distilled off from the solution and the residue is dissolved in a mixed solvent comprising benzene-hexane (1:4) and the resulting solution is subjected to a 15 to 20 fold amount of silica gel column. Elution is effected with the above benzene-hexane mixed solvent and the fore-running is separated. This portion which comprises a mixture of 13-cis compound and 9-cis compound is subjected again to the column under the same condition as above to separate the 13-cis compound alone. There is obtained oily yellow α-tocopherol-13-cis-vitamin A acid ester. The above separation step is preferably carried out under shading.

FORMULATION EXAMPLE 1

25 g Of α-tocopherol vitamin A acid ester and 7.5 g of polyoxyethylene castor oil (Nikkol HCO 60 ®) are dissolved in acetone and then 25 g of anhydrous silicic acid are mixed. After evaporation of acetone, 5 g of carboxymethyl cellulose calcium, 5 g of corn starch, 7.5 g of hydroxypropyl cellulose (HPO-L ®) and 20 g of fine crystal cellulose are mixed and the resulting mixture is kneaded with the addition of 30 ml of water and then granulated in a granulating machine equipped with No. 24 mesh (B.S.) screen (Eck pelleter, manufactured by Fuji Paudal K.K.). Granules thus obtained are dried up to less than 5% of moisture and passed through a sieve of No. 16 mesh (B.S.). Subsequently, these granules are encapsulated by means of an encapsulating machine at the proportion of 190 mg per capsule.

FORMULATION EXAMPLE 2

Soft capsules for oral administration 50 g Of α-tocopherol vitamin A acid ester and 130 g of fractionated coconut oil (Miglyol 812 ®) are mixed to give a homogeneous solution. Separately, a gelatin solution having the composition comprising 93 g of gelatin, 19 g of glycerin, 10 g of D-sorbitol, 0.4 g of ethyl para-hydroxybenzoate, 0.2 g of propyl para-hydroxybenzoate and 0.4 g of titanium oxide is prepared and used as capsule film. According to the manual plate process, soft capsules containing 180 mg of contents are prepared.

FORMULATION EXAMPLE 3

Injections 5 g Of α-tocopherol vitamin A acid ester, an appropriate amount of peanut oil and 1 g of benzyl alcohol are mixed and further peanut oil is added to make up the total 100 cc. The resulting solution is sterilizedly charged into an ampoule in the amount of 1 cc and then the ampoule is melt closed.

I claim:

1. A method of treating tumors in patients, which comprises administering to said patients an antitumor composition containing, as active ingredient, an antitumor effective amount of an α-tocopherol vitamin A acid ester in a pharmaceutical carrier.

2. A method according to claim 1 wherein the antitumor active ingredient is selected from a group consisting of α-tocopherol trans-vitamin A acid ester and α-tocopherol-13-cis-vitamin A acid ester.

* * * * *